United States Patent [19]
Matsutani et al.

[11] Patent Number: 5,473,096
[45] Date of Patent: Dec. 5, 1995

[54] SUBSTITUTED BENZOATE DERIVATIVES

[75] Inventors: Shigeru Matsutani, Hashimoto; Tadashi Yoshida, Toyono; Ryuji Sakazaki, Nara; Yasuhiko Fujii, Kobe; Kazushige Tanaka, Nishinomiya, all of Japan

[73] Assignee: Shionogi & Co., Ltd., Osaka, Japan

[21] Appl. No.: 93,953

[22] Filed: Jul. 21, 1993

[30] Foreign Application Priority Data

Jul. 23, 1992 [JP] Japan ................................ 4-196789

[51] Int. Cl.⁶ .................... C07C 229/36; A61K 31/24
[52] U.S. Cl. ................ 560/39; 560/27; 560/42
[58] Field of Search ............... 560/39, 42, 66, 560/27; 514/533, 539, 544, 486

[56] References Cited

U.S. PATENT DOCUMENTS 5,011,952  4/1991  Yoshida et al. ..................... 549/393

FOREIGN PATENT DOCUMENTS 0395418  10/1990  European Pat. Off. .
0547231  6/1993  European Pat. Off. .
1415266  11/1975  United Kingdom .

OTHER PUBLICATIONS

Patent Abstracts of Japan, vol. 16, No. 449 (C–986), Sep. 18, 1992.
Patent Abstracts of Japan, vol. 16, No. 362 (C–971), Aug. 5, 1992.
Patent Abstracts of Japan, vol. 17, No. 309 (C–1070), Jun. 14, 1993.
Patent Abstracts of Japan, vol. 16, No. 449 (C–986), Sep. 18, 1992.

*Primary Examiner*—Jose G. Dees
*Assistant Examiner*—Barbara S. Frazier
*Attorney, Agent, or Firm*—Wenderoth, Lind & Ponack

[57] ABSTRACT

The present invention relates to the compounds of the formula:

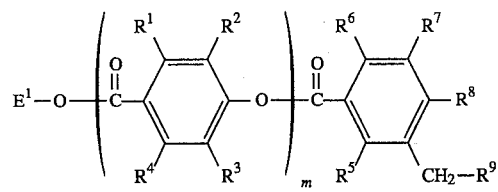

in which $R^1$, $R^2$, $R^3$, $R^4$, $R^5$, $R^6$, $R^7$, and $R^8$ are independently hydrogen, lower alkyl which is optionally substituted, lower alkoxy which is optionally substituted, hydroxy, acyloxy, or halogen; $R^9$ is hydrogen, hydroxy, acyloxy, lower alkyl which is optionally substituted, lower alkoxy which is optionally substituted, or lower alkylamino which is optionally substituted; $E^1$ is hydrogen, or an ester residue; m is an integer of from 1 to 4;
or a pharmaceutically acceptable salt thereof. The compounds of the present invention exhibit phospholipase $A_2$ inhibitory activity, and can be used in treating inflammatory conditions.

4 Claims, No Drawings

SUBSTITUTED BENZOATE DERIVATIVES

FIELD OF THE INVENTION

The present invention relates to novel phospholipase $A_2$ inhibitors. In more particular, the present invention relates to novel compounds exhibiting an inhibiting effect on phospholipase $A_2$, which compounds are analogs of biologically active substances, thielocins which are produced by microorganisms such as *Thielavia, terricola* RF-143 belonging to Thielavia genus.

THE PRIOR ART

Phospholipase $A_2$ is an enzyme which exists in a cell and a secretory liquid, in particular, a venom of snakes, pancreas of a mammal, blood platelets of various animals, arthritis exudate of higher animals, and so on. The enzyme specifically hydrolyses phospholipids. For example, the enzyme specifically hydrolyses C-2 fatty acid esters of 1,2-diacylglycerol phospholipids to form lysoglycerophospholipids and fatty acids. Phospholipid $A_2$ exhibits toxicity on nerve, muscle and heart, and anticoagulant actions in association with the above enzymatic action, and it is generally said that the enzyme may induce convulsant, hypotonia, haemolysis, bleeding, edema, and so on. Further, the enzyme can also be directly or indirectly responsible for other clinical symptoms including inflammations. It should be noted that phospholipase $A_2$ is recognized to be one of the phlogogenic substances in human.

If the enzymatic activity of phospholipase $A_2$ which is the phlogogenic substance can be inhibited, various diseases caused by or associated with the enzymatic activity can probably be treated. Based on such assumption, substances such as mepacrine and p-bromophenacyl bromide have already been developed, and the applicants have also disclosed and claimed novel phospholipase $A_2$ inhibitors in European Patent Application Nos. 90304552-4, 92913882-4, Japanese Patent Application No. 234955/1990. However, it is desirable to develop additional phospholipase $A_2$ inhibitors, because types of the phospholipase $A_2$ molecules are varied and the activity of one of the molecules is not the same as the other due to the difference of the structure of the molecules.

DESCRIPTION OF THE PRESENT INVENTION

The applicants have filed the Japanese patent applications which disclose and claim various useful thielocin derivatives, which are produced by chemical synthesis. Now, the applicants have chemically synthesized new thielocin derivatives having lower molecular weight, using thielocin B groups among the various thielocin derivatives as lead compounds, and established the present invention.

Specifically, the present invention relates to substituted benzoates derivatives of the formula:

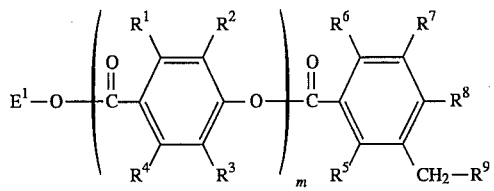

in which $R^1$, $R^2$, $R^3$, $R^4$, $R^5$, $R^6$, $R^7$, and $R^8$ are independently hydrogen, lower alkyl which is optionally substituted, lower alkoxy which is optionally substituted, hydroxy, acyloxy, or halogen;

$R^9$ is hydrogen, hydroxy, acyloxy, lower alkyl which is optionally substituted, lower alkoxy which is optionally substituted, or lower alkylamino which is optionally substituted, preferably $R^9$ is a group which is selected from the group consisting of:

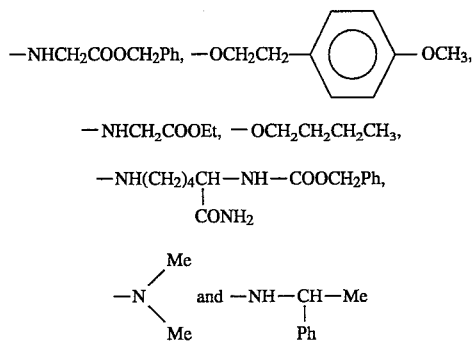

wherein Ph is an optionally substituted phenyl group;

$E^1$ is hydrogen, or an ester residue;

m is an integer of from 1 to 4;

or pharmaceutically acceptable salts thereof.

Several terms used in the present specification are defined below:

The term "lower alkyl" refers to $C_1$–$C_6$ alkyl such as methyl, ethyl, propyl, isopropyl, butyl, isobutyl, tert-butyl, pentyl, hexyl, and so on.

The term "lower alkoxy" refers to $C_1$–$C_6$ alkoxy such as methoxy, ethoxy, propoxy, isopropoxy, butoxy, isobutoxy, tert-butoxy, pentoxy, hexyloxy, and so on.

The term "acyloxy" refers to acetyloxy, propionyloxy, butyryloxy, and so on.

The term "halogen" refers to chlorine, bromine, iodine, or fluorine.

The term "ester residue" refers to an alkyl having 1 to 8 carbon atoms (methyl, methoxymethyl, ethyl, ethoxymethyl, iodoethyl, propyl, isopropyl, butyl, isobutyl, ethoxyethyl, methylthioethyl, methanesulfonylethyl, trichloroethyl, t-butyl, and so on), an alkenyl having 3 to 8 carbon atoms (propenyl, allyl, butenyl, hexenyl, phenylpropenyl, dimethylhexenyl, and so on), an aralkyl having 7 to 19 carbon atoms (benzyl, methylbenzyl, dimethylbenzyl, methoxybenzyl, ethoxybenzyl, nitrobenzyl, aminobenzyl, diphenylmethyl, phenylethyl, trityl, di-t-butylhydroxybenzyl, phthalidyl, phenacyl, and so on), an aryl having 6 to 12 carbon atoms (phenyl, tolyl, methoxyphenyl, diisopropylphenyl, xylyl, trichlorophenyl, pentachlorophenyl, indanyl, and so on), an N-hydroxyamino compound having 1 to 12 carbon atoms (acetone oxime, acetophenone oxime, acetaldoxime, N-hydroxy succinimide, N-hydroxy phthalimide, and so on), a hydrocarbonated silyl having 3 to 12 carbon atoms (trimethylsilyl, dimethylmethoxysilyl, t-butyldimethylsilyl, and so on), a hydrocarbonated stannyl having 3 to 12 carbon atoms (trimethyl stannyl, and so on), mono-oxygenated alkyl having 2 to 15 carbon atoms [a straight, branched, cyclic or partially cyclic alkanoyloxyalkyl (acetoxymethyl, acetoxyethyl, propionyloxymethyl, pivaloyloxymethyl, pivaloyloxyethyl, cyclohexanacetoxyethyl, cyclohexanecarbonyloxycyclohexylmethy, and so on), an alkoxycarbonyloxyalkyl having 3 to 15 carbon atoms (ethoxycarbonyloxyethyl, isopropoxycarbonyloxyethyl, isopropoxycarbonyloxypropyl, t-butoxycarbonyloxyethyl, isopentyloxycarbonyloxypropyl, cyclohexyloxycarbonyloxyethyl, cyclohexylmethoxycarbonyloxyethyl, bornyloxycarbonyloxyisopropyl, and so on), an alkoxyalkyl having 2 to 8 carbon atoms (methoxymethyl, methoxyethyl, and so on), 2-oxacycloalkyl having 4 to 8 carbon atoms (tetrahydropyranyl, tetrahydrofurany ester, and so on), and so on], a substituted aralkyl having 8 to 12 carbon atoms (phenacyl, phthalidyl, and so on), an aryl having 6 to 12 carbon atoms (phenyl, xylyl, indanyl, and so on), an alkenyl having 2 to 12 carbon atoms (allyl, (2-oxo-1,3-dioxolyl) methyl, and so on), and so on.

The term "a lower alkylamino which is optionally substituted" refers to an alkylamino which may have one or more substituent(s) which are identically or differently selected from an aryl group, an amino group of an urethane derivative, and a carboxyl group which may be esterified or amidated.

The term "an urethane derivative" described above includes ethyl carbamate, methyl carbamate, propyl carbamate, ammonium carbamate, phenyl carbamate, and benzyl carbamate, and, in the present invention, benzyl carbamate which is optionally substituted is most preferred.

Further, "a carboxyl group which may be esterified" includes carboxyl group, methoxycarbonyl group, ethoxycarbonyl group, tert-butoxycarbony group, benzyloxycarbonyl group, and so on and, in the present invention, ethoxycarbonyl group and benzyloxycarbonyl group are most preferred.

The term "a lower alkyl which is optionally substituted" refers to an alkyl optionally substituted by one or more substituent(s) which are the same or different and which are selected from lower alkoxy, halogen, hydroxy, amino, and aryl which is optionally substituted, and a preferred substituent includes methoxy, ethoxy, hydroxy, and so on. An aryl includes phenyl, naphthyl, anthryl and so on.

The term "a lower alkoxy which is optionally substituted" refers to an alkoxy optionally substituted by one or more substituent(s) which are the same or different and which are selected from lower alkyl, halogen, hydroxy, amino, and aryl which is optionally substituted, and a preferred substituent includes aryl which is optionally substituted. The most preferred substituent is a phenyl which is substituted by a lower alkoxy such as methoxy, and ethoxy.

The term "an optionally substituted phenyl group" refers to a phenyl group which may have one or more substituents which are identically or differently selected from the group of halogen, lower alkoxy, hydroxy, amino and aryl which is optionally substituted.

The compounds of the present invention can form salts with a metal such as an alkali metal (sodium, potassium, etc.), or an alkaline earth metal (calcium, etc.) capable of forming a salt with a carboxylic acid.

The compounds of the present invention can be prepared in accordance with preparations A, and B of the following scheme:

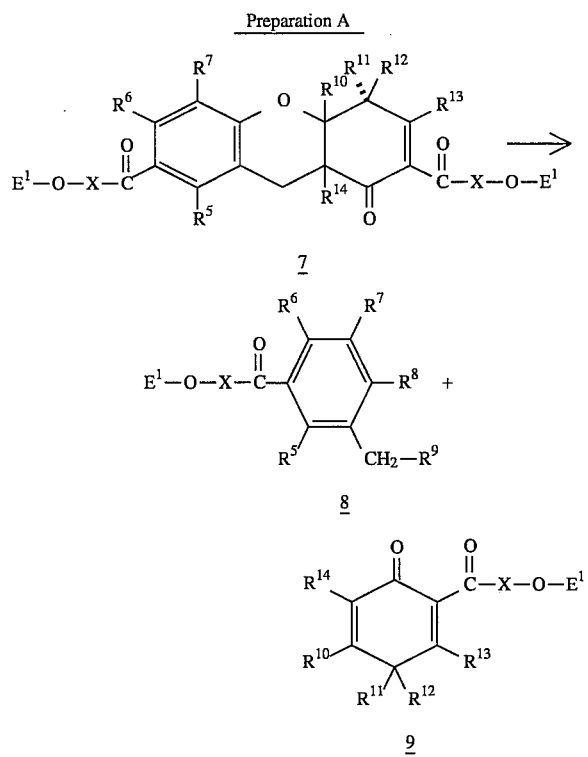

Preparation A

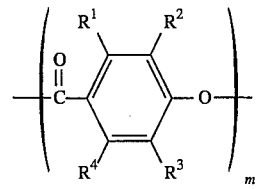

wherein $R^1$, $R^2$, $R^3$, $R^4$, $R^5$, $R^6$, $R^7$, $R^8$, $R^9$, m, and $E^1$ are as defined above, $R^{10}$, $R^{11}$, $R^{12}$, $R^{13}$, and $R^{14}$ are independently hydrogen, lower alkyl, and hydroxy group.

Compound 7 is reacted with a suitable amine or alcohol in a suitable solvent at −50° C. to 100° C., preferably at 0° C. to about room temperature, and preferably in the presence of a base to yield compounds 8 and 9.

As an amine, aliphatic amines such as methylamine, ethylamine, propylamine, dimethylamine, diethylamine, and so on, aromatic amines such as aniline, methylaniline, dimethylaniline, and so on, and amino acids such as glycine or ester thereof, lysine or ester thereof, and so on are used.

As an alcohol, methanol, ethanol, glycinebenzyloxytosyl alcohol, or p-methoxy-2-phenyl ethanol, and so on are used.

As a base, potassium hydroxide, sodium hydroxide, calcium hydroxide, potassium carbonate, triethylamine, pyridine, and so on are used.

As a solvent, alcohols such as methanol, ethanol, and so on, dioxane, tetrahydrofuran, DMF, DMSO, or an aqueous mixture therewith may be used.

Preparation B ($R^9$ is a alkylamino)

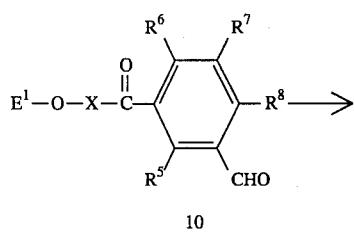

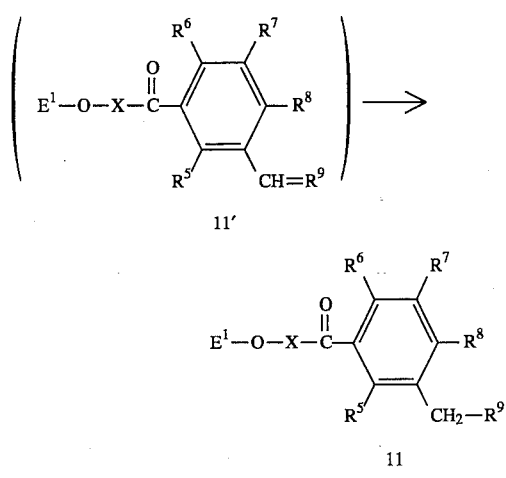

wherein $R^5$, $R^6$, $R^7$, $R^8$, X, and $E^1$ are as defined above. Compound 10 is reacted with $R^9H$ in the presence of a reducing agent such as a borohydride, for example, sodium borohydride to yield compound 11, and if necessary, the latter is subjected to deprotection.

The reaction is conducted in a suitable solvent at −50° C. to 50° C., preferably at −20° C. to about room temperature, preferably in a stream of nitrogen.

Alcohols such as methanol, ethanol, and so on, acetic acid, trifluoroacetic acid, benzene, toluene, ether, tetrahydrofuran, tetrahydropyridine, and pyridine, and so on are used as a suitable solvent.

When, in this process, compound 11' may be formed before compound 11 is prepared, then compound 11' is reduced to yield compound 11. The reduction is conducted using the reducing agent previously described herein. Alternatively, the reduction can be also conducted using sodium cyanohydride, etc., or by catalytic reduction. This catalytic reduction is conducted in accordance with the conventional procedure using platinum, palladium, nickel, cobalt, iron, copper, etc.,.

The compounds of the present invention can be formulated into oral or external preparations in association with various carriers. Dose of the compounds will differ depending on the intended treatment effect, the administration route, and age and body weight of particular patients, and therefore, the dose cannot be defined in general. Usually, daily dose may be about 0.1 mg to about 500 mg, preferably about 0.5 mg to about 100 mg in the case of oral administration. On the administration, the above dose may be divided into one to five portions.

Typical examples of the compounds of the present invention, which are shown in the above formula are illustrated below:

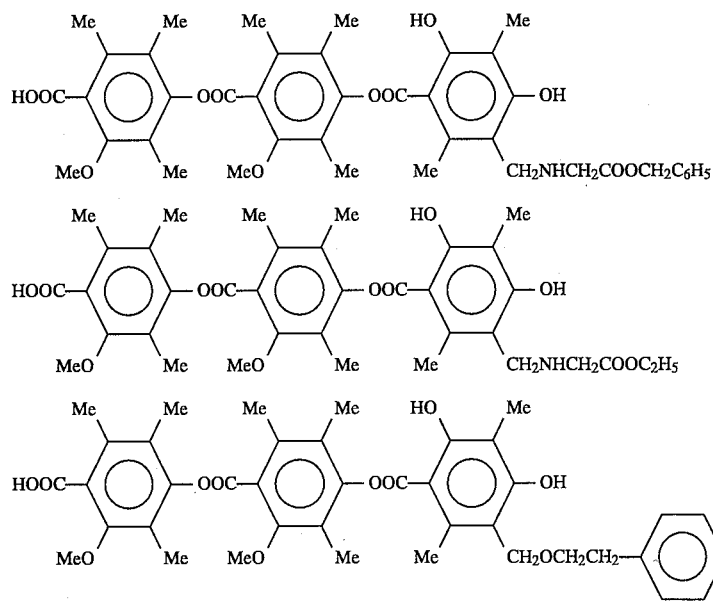

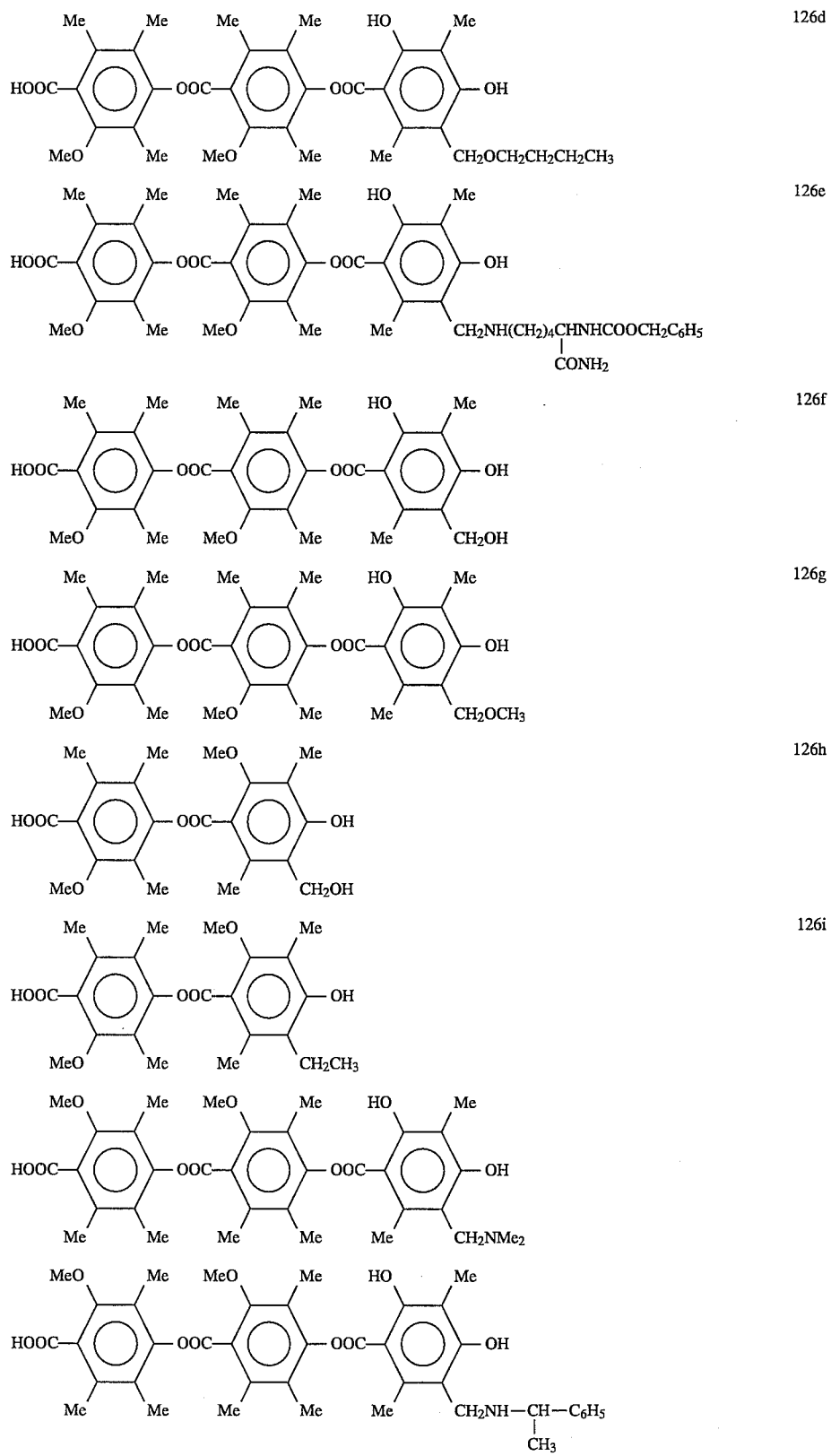
All of the compounds of the present invention can be prepared by methods which are known in the art.
The following examples and preparations are provided to further illustrate the process for preparing the compounds of the invention. The examples and preparations are representative only, and should not be construed as limiting the invention in any respect.

Example

Example 1

4-[4'-(4"-Carboxy-3"-methoxy-2",5",6"-trimethylphenoxycarbony)-3'-methoxy-2',5',6'-trimethylphenoxycarbonyl]-2,5-dimethyl-6-benzyloxyglycylmethylresorcinol (1a)

Thielocin A2α (2a) [This compound was prepared in accordance with the procedure of Japanese Patent Publication (kokai) 158790/1992] (12 mg) was dissolved in 1 ml of dioxane, and to the solution were added subsequently glycine benzyl ester p-toluenesulfonate (10 mg), two drops of triethylamine, and 0.2N NaOH (2 ml) with stirring, and then the mixture was stirred at room temperature for one hour. The reaction mixture was diluted with water, acidified to pH 3.0 with dilute hydrochloric acid, and the mixture was extracted with ethyl acetate. The extract was dried over $Na_2SO_4$, and the solvent was evaporated in vacuo to yield a residue. The residue was subjected to thin layer chromatography on silica gel developing with $CHCl_3$:methanol:water= 62:25:2, to isolate a desired material (Rf: 0.6). Then, the material was purified by high performance liquid chromatography (Nucleosil $5C_{18}$, 80% acetonitrile-0.1% $H_3PO_4$) to yield 1.5 mg of the title compound ($t_R$(min.) 8.0).

$^1$H-NMR: described hereinafter MS spectrum: MH+m/z Found: 744 (Theory: 744 for $C_{41}H_{45}NO_{12}$).

The above reaction is described as shown in the following scheme:

wherein X is a group of the formula:

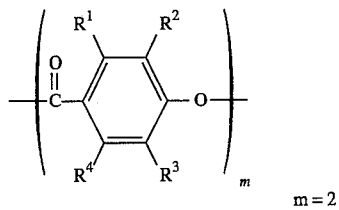

$m = 2$ $R^1$, $R^2$ and $R^3$ are methyl, $R^4$ is methoxy, $R^5$ and $R^7$ are methyl, $R^6$ is hydroxy, $R^8$ is hydroxy, $R^9$ is —$NHCH_2CO_2CH_2C_6H_5$, $R^{10}$ and $R^{11}$ are hydroxy, and $R^{12}$, $R^{13}$ and $R^{14}$ are methyl, and $E^1$ is hydrogen.

Examples 2–9

Thielocin A2α (2a) or A1α [2b, which is described in the specification of the European Patent Application No. 90304552-4] was reacted with various compounds of $RNH_2$ or ROH instead of glycine benzyloxy ester, and treated in a similar procedure to that of Example 1, to yield compounds 1b through 1i. Such reactions are shown in the following scheme.

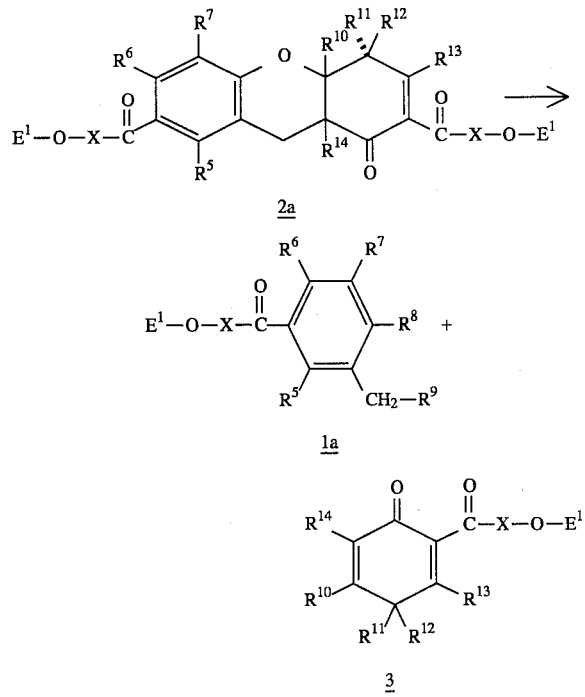

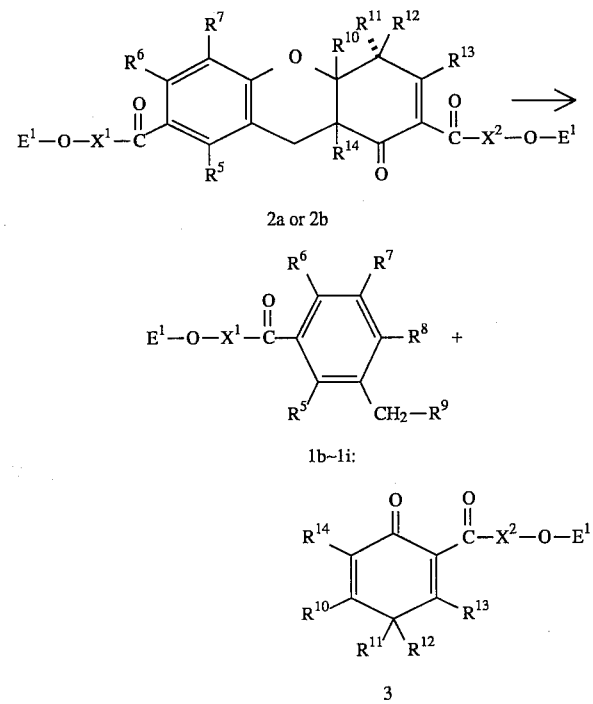

wherein $X^1$ is a group of the formula:

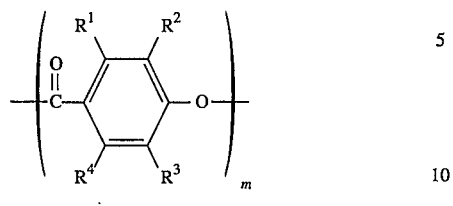

$X^2$ is a group of the formula:

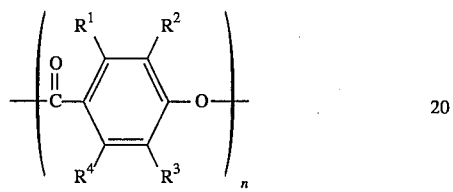

$R^1, R^2, R^3, R^4, R^5, R^6, R^7, R^8, R^9, R^{10}, R^{11}, R^{12}, R^{13}, R^{14}$, and $E^1$ are as defined above;
provided that m=n=2 in the case of compound 2a, and that m=1 and n=2 in the case of compound b.

Conditions of such reaction, and chemical formula of the compounds are shown in Tables 1 and 2, respectively. Also, physical properties of compounds 1 a to 1i are shown in Table 3.

TABLE 1

| Compound No. | | (2)(mg) | RNH₂/ROH | (mg) | base/solvent | Reaction time | yield | *Rf |
|---|---|---|---|---|---|---|---|---|
| 1 b | a | 12 | NH₂CH₂CO₂C₂H₅·HCl | 20 | 2 ml 0.2N — NaOH/dioxane | 1 ml 30 min. 0.6 | 3 mg | 0.5 |
| 1 c | a | 10 | HOCH₂CH₂O–⟨C₆H₄⟩–Me | 100 | 0.5 ml 0.2N — NaOH/dioxane | 1 hr. | 2.5 mg | 0.6 |
| 1 d | a | 10 | HOCH₂CH₂CH₂CH₃ | 400 | 0.5 ml 0.2N — NaOH/n-BnOH | 0.5 ml 1 hr. | 1 mg | 0.7 |
| 1 e | a | 12 | NH₂(CH₂)₄CONHCO₂CH₂C₆H₅ \| CONH₂ | 15 | 1 ml 0.2N — NaOH/dioxane | 1 ml 20 min. | 4 mg | 0.4 |
| 1 f | a | 13 | — | | 1 ml 0.2N — NaOH/dioxane | 1 ml 20 min. | 3 mg | 0.6 |
| 1 g | a | 10 | CH₃OH | | 1 ml 0.2N — NaOH/aq. MeOH | 1 ml 30 min. | 3 mg | 0.7 |
| 1 h | b | 11 | — | | 0.2N — NaOH/dioxane | 1 hr. | 2.1 mg | 0.2 |
| 1 i | b | 10 | CH₃OH | | 1 ml 0.2N — NaOH/aq. MeOH | 1 ml 1 hr. | 2 mg | 0.3 |

*KGF₂₅₄60(Merck); CHCl₃:H₂O(62:25:2, v/v/v)

TABLE 2
| Compound No. | $R^6$ | $-X-O-E^1$ | $R^9$ |
|---|---|---|---|
| 1 b | H, | 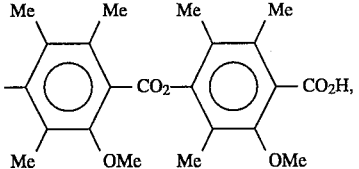 | $-NHCH_2CO_2C_2H_5$ |
| 1 c | H, | 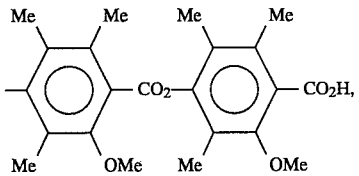 | $-OCH_2CH_2$—⟨phenyl⟩—$OCH_3$ |
| 1 d | H, |  | $-OCH_2CH_2CH_2CH_3$ |
| 1 e | H, | 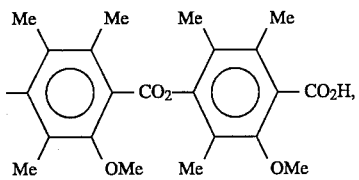 | $-NH-(CH_2)_4CHNHCO_2CH_2C_6H_5$<br>            $\|$<br>         $CONH_2$ |
| 1 f | H, | 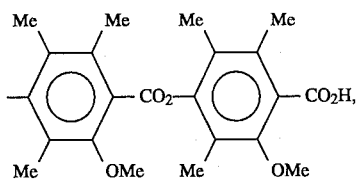 | OH |
| 1 g | H, | 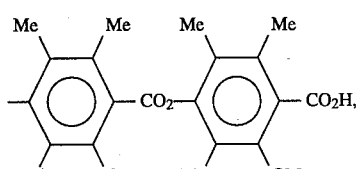 | $OCH_3$ |
| 1 h | Me, | 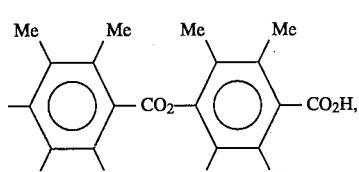 | OH |
| 1 i | Me, | 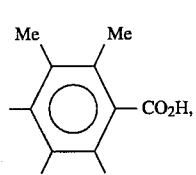 | H |

TABLE 3

| Compound No. | Molecular Formula | SIMS MH m/z | $^1$H-NMR(CDCl$_3$) |
|---|---|---|---|
| 1a | C$_{41}$H$_{45}$NO$_{12}$ | 744 | δ2.12, 2.14, 2.15, 2.17, 2.26, 2.29, 2.36, 2.41, 2.59(3Hs each, CH$_3$), δ3.60(2Hs, COC$\underline{H}_2$NH), 4.17(2Hs, ArC$\underline{H}_2$NH), 5.23 (2Hs, O—C$\underline{H}_2$ph), δ7.37(5Hs, ph) |
| 1b | C$_{36}$H$_{43}$NO$_{12}$ | 682 | δ1.32(3Ht, J=7.0Hz, CH$_2$C$\underline{H}_3$), δ2.31, 2.51, 2.18, 2.26, 2.26, 2.29, 2.36, 2.41, 2.62 (3Hs each, CH$_3$), 3.50(2Hs, COC$\underline{H}_2$NH), δ3.85, 3.86(3Hs each, OCH$_3$), δ4.13(2Hs, ArC$\underline{H}_2$NH), δ4.27(2Hz, J=7.0Hz, C$\underline{H}_2$CH$_3$). |
| 1c | C$_{41}$H$_{46}$O$_{12}$ | 731 | δ2.12, 2.13, 2.18, 2.26, 2.29, 2.36, 2.42, 2.61(3Hs each, CH$_3$). |
|  |  | 753 (MNa$^+$) | δ2.93, 3.80(2Ht, J=7.0Hz, CH$_2$), δ3.81, 3.85, 3.86(3Hs each, OCH$_3$), δ4.83(2Hs, ArC$\underline{H}_2$O), δ6.87, 7.16(2Hd each, J=8.8Hz. =$\langle^H_{\ }\rangle$). |
| 1d | C$_{36}$H$_{44}$O$_{11}$ | 675 (MNa$^+$) | δ0.96(3Ht, J=7.1 Hz, (CH$_2$)$_3$C$\underline{H}_3$), δ2.13, 2.16, 2.18, 2.26, 2.29, 2.36, 2.41, 2.62(3Hs each, CH$_3$), 1.45, 1.66(2Hm each, CH$_2$), 3.63(2Ht, J=7.6Hz OCH$_2$(CH$_2$)-), δ3.85, 3.86(3Hs each, OCH$_3$), 4.84(2Hs, ArC$\underline{H}_2$O). |
| 1e | C$_{46}$H$_{55}$N$_3$O$_{13}$ | 858 | δ2.12, 2.15, 2.16, 2.22, 2.25, 2.28, 2.39, 2.65(3Hs each, CH$_3$), δ3.83(6Hs, OCH$_3$), δ4.15(2Hs, NHC$\underline{H}_2$Ar), δ5.11(2Hs, CO$_2$C$\underline{H}_2$ph), δ7.34(5Hz, ph) |
| 1f | C$_{32}$H$_{36}$O$_{11}$ | 597 | δ2.13, 2.16, 2.18, 2.23, 2.27, 2.30, 2.41, 2.63(3Hs each, CH$_3$), δ3.83, 3.84(3Hs each, OCH$_3$), 4.98(2Hs-C$\underline{H}_2$OH) |
| 1g | C$_{33}$H$_{38}$O$_{11}$ | 611 | δ2.13, 2.16, 2.18, 2.26, 2.29, 2.36, 2.42, 2.64(3Hs each, CH$_3$), δ3.52(3Hs, CH$_2$OC$\underline{H}_3$), δ3.85, 3.86(3Hs each, OC$\underline{H}_3$), δ4.81 (2Hs, C$\underline{H}_2$OCH$_3$) |
| 1h | C$_{22}$H$_{26}$O$_8$ | 419 | δ2.22, 2.24, 2.27, 2.34. 2.35(3Hs each, CH$_3$), 3.51(3Hs, CH$_2$OC$\underline{H}_3$), δ3.83, 3.86(3Hs each, OC$\underline{H}_3$), δ4.77(2Hs, C$\underline{H}_2$OCH$_3$) |
| 1i | C$_{23}$H$_{28}$O$_8$ | 433 | [δ2.22(6Hs, 2×CH$_3$), δ2.24, 2.29, 2.33(3Hs each, CH$_3$), δ3.83(6Hs, 2×OCH$_3$), δ4.91 (2Hs, C$\underline{H}_2$OH)]* |

Example 10

4-[4'-[5''-(Dimethylaminomethyl)-2'',4''-dihydroxy-3'',6''-dimethylphenylcarboxyl]-2'-methoxy-3',5',6'-trimethyl]phenylcarboxy-2-methoxy-3,5,6-trimethyl benzoic acid (6a)

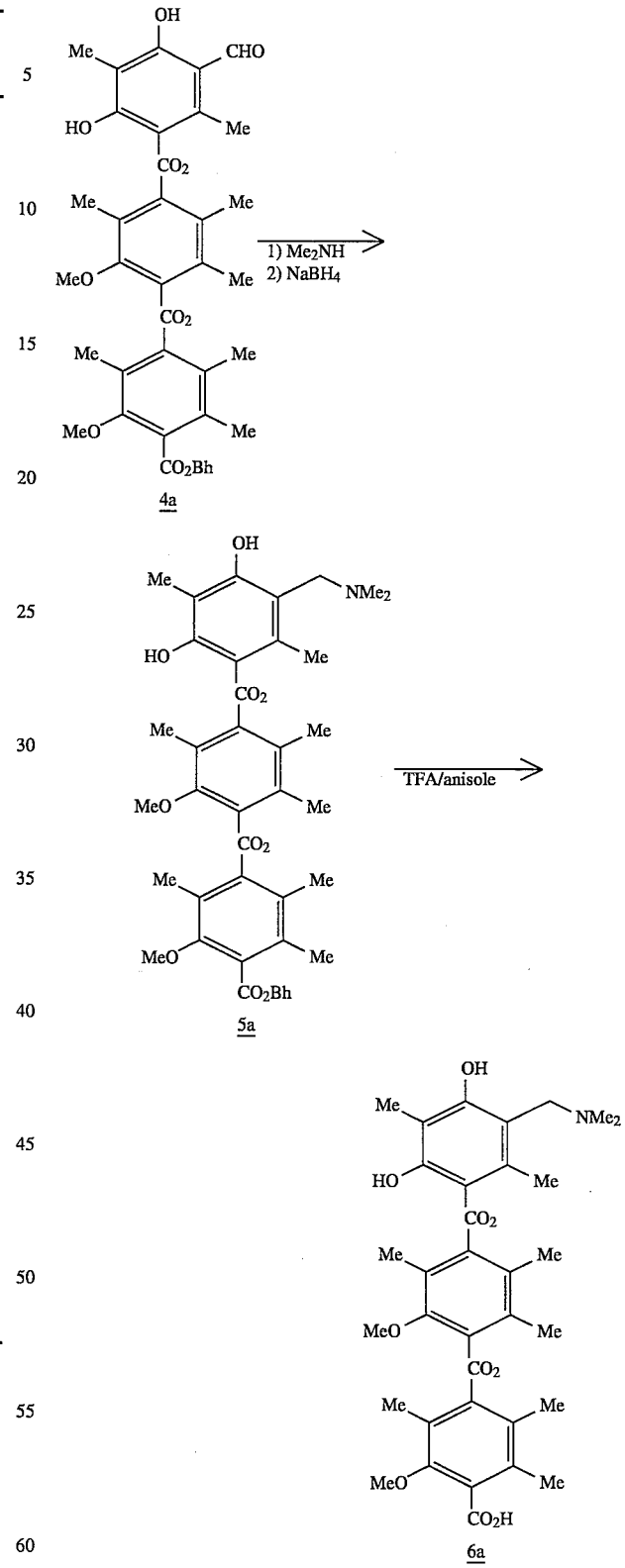

In the reaction scheme above, Bh means benzhydryl.

To a solution of 10.7 g (130 mmol) of dimethylamine hydrochloride in 200 ml of methanol is added 20.3 g (105 mmol) of NaOMe (in methanol, 28%) at −10° C. to −15° C. over about five minutes in a stream of nitrogen. After the mixture was stirred for 40 minutes, 4a (1 g, 1.3 mmol), which had been synthesized in Preparation 1 hereinafter was added thereto, and the resulting mixture was allowed to warm to 0° C., and stirred for 2.5 hours. To the mixture was added a portion of 60 mg (1.6 mmol) of 500 mg (13 mmol) of $NaBH_4$ over 10 minutes, and then the remainder of $NaBH_4$ was added thereto together. After stirring for 40 minutes, the mixture was allowed to stand overnight at room temperature. The solvent, methanol, was evaporated, and the residue was distributed between ethyl acetate and water. The ethyl acetate layer was washed with water and brine, and then dried over $Na_2SO_4$. The solvent was evaporated to yield 1.31 g of a residue. The residue was subjected to column chromatography (SiO; 100 g), washing with ethyl acetate-hexane (1:1), and then eluting with $CHCl_3$-methanol (20:1), to yield 1 g of the product as a pale brown oil. The oil was crystallized from methanol to yield 844 mg of 5a (the benzhydryl ester of 6a) as a white powder (81.3%).

Then, 120 mg (1.11 mmol) of anisole was added to a solution of 5a (200 mg, 0.26 mmol) in 5 ml of dichloromethane, and the mixture was cooled to 0° C. To the mixture was added 1 ml of a solution of 300 mg of trifluoroacetic acid in dichloromethane, and the resulting mixture was stirred at 0° C. for one hour. After stirring, the mixture was allowed to stand overnight in the refrigerator at 4° C., and the solvent was evaporated to yield 0.46 g of a residue as a pale yellow oil. The residue was crystallized from ether, and the crystals were collected by filtration, and recrystallized from ethanol-water to yield 63 mg of the desired compound 6a (39.9%).

Mp: 218°–220° C. (dec.)

6a

Molecular formula: $C_{34}H_{41}NO_{10}$ SIMS: MH+m/z 624
$^1$H-NMR ($CDCl_3$) δ2.14, 2.16, 2.19, 2.24, 2.27, 2.29, 2.42, 2.67 (3Hs each, $CH_3$), δ2.57 (6Hs, $NMe_2$), δ3.99 (2Hs, ArC$\underline{H}_2$N)

Example 11

4-[4'-[5"-(Sec-phenethylaminomethyl)-2",4"-dihydroxy-3", 6"-dimethylphenylcarboxy]-2'-methoxy-3',5',6'-trimethyl] phenylcarboxy-2-methoxy-3,5,6-trimethyl benzoic acid (6b)

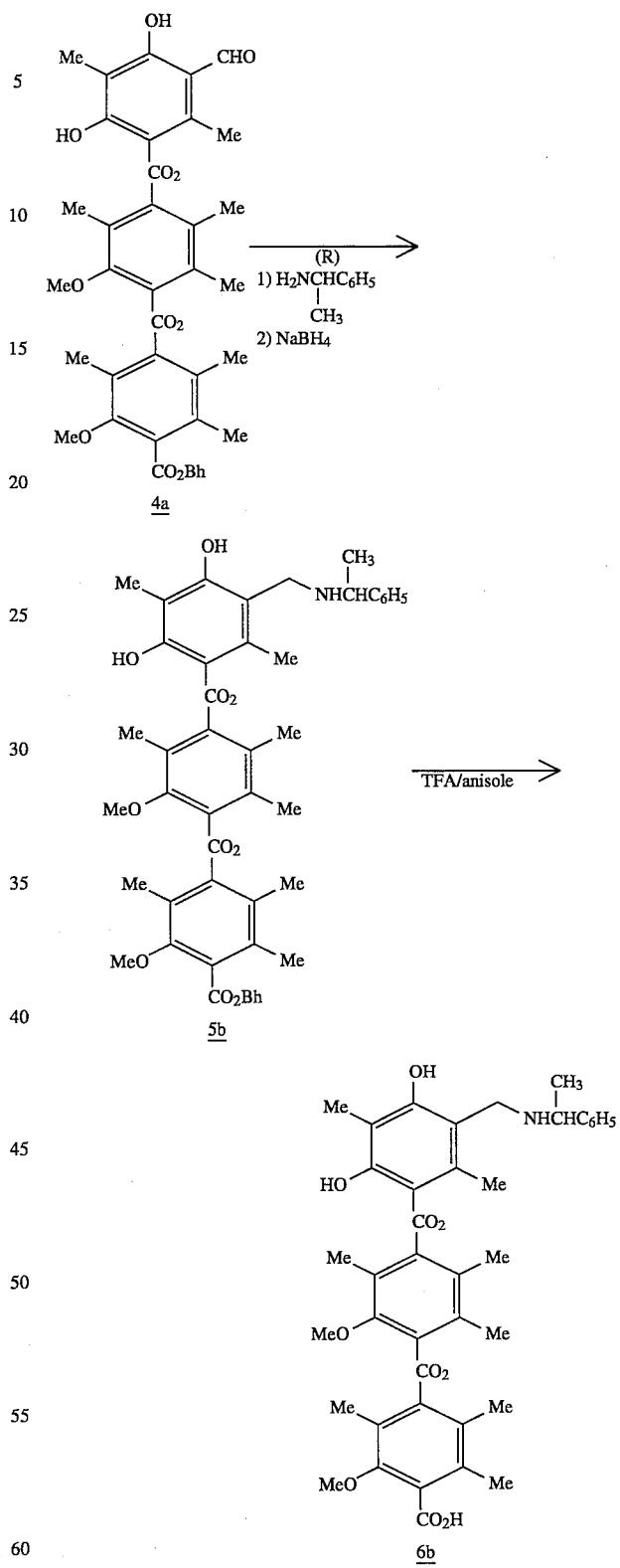

Three hundred mg of 4a (Preparation 1) was reacted in a similar procedure to that of Example 10 except that 658 mg of a compound of $C_6H_5CH(CH_3)NH_2$ (sec-phenethylamine) was used instead of $Me_2HN$, and that 80 mg of $NaBH_4$ was reacted in 2.5 ml of DMF and 12 ml of methanol, to yield 314 mg of 5b (the benzhydryl ester of the desired compound 6b).

Then, to a solution of the resulting compound 5b in dichloromethane (10 ml) were added 180 mg of anisole and 420 mg of trifluoroacetic acid, and the mixture was reacted in a similar procedure to that of Example 10, to yield 136 mg of the title compound 6b.

6b

Molecular formula: $C_{40}H_{45}NO_{10}$ SIMS: MH+m/z 700 $^1$HNMR (CDCl$_3$) [δ1.57 (3Hd, J=6.8 Hz), δ2.13 (3Hs, CH$_3$), δ2.15 (6Hs, CH$_3$), δ2.23, 2.26, 2.29, 2.40, 2.42 (3Hs, each CH$_3$), δ3.83, 3.84 (3Hs each, OCH$_3$), 3.94 (2Hm, ArC$\underline{H}_2$NH), 7.37 (5Hm, C$_6$H$_5$)]

Example 12

Step 1

Benzhydryl 4-[4'-[5"-(benzyloxycarbonymethyliminomethyl)-2",4"-dihydroxy-3",6"-dimethylphenylcarboxy]-2'-methoxy-3',5',6'-trimethyl]phenylcarboxy-2-methoxy-3,5,6-trimethyl benzoate (5c)

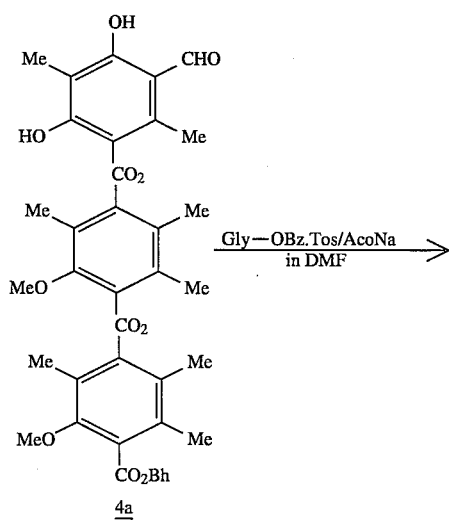

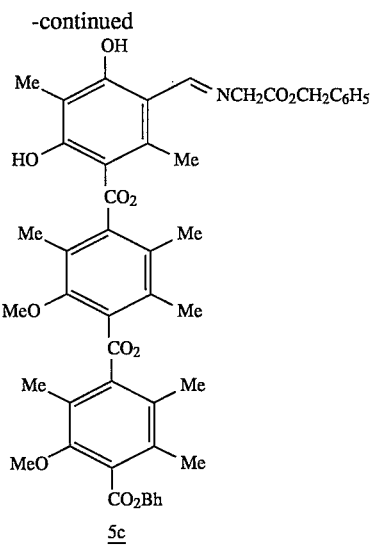

Two g (2.6 mmol) of 4a (Preparation 1) and 8.9 g (26 mmol) of glycine benzyl ester p-toluenesulfonate were dissolved in 30 ml of a dried dimethylformamide, and then to the solution was add 4.3 g (52 mmol) of sodium acetate, and the mixture was stirred for 3.5 hours. The reaction mixture was poured into 300 ml of cooled water to precipitate crystals, which were collected by filtration. The crystals were dissolved in 100 ml of ethyl acetate, and the solution was washed with 100 ml of water and 100 ml of brine, then dried over anhydrous sodium sulfate. The solvent was evaporated to yield 2.58 g of the title compound 5c as an yellow foamy material. The material was recrystallized from ethyl acetate-n-hexane (1:2) to yield 2.2 g of the desired compound (92.2%) as yellow pillar crystals.

Mp: 153°–5° C. Elementary Analysis (for $C_{54}H_{53}NO_{12}$ (MW 907.972)) Theory: C;71.43, H;5.88, N;1.54 Found: C;71.69, H;5.88, N;1.62

Step 2

4-[4'-[5"-(Benzyloxycarbonylmethylaminomethyl)-2",4"-dihydroxy-3",6"-dimethylphenylcarboxy]-2'-methoxy-3',5', 6'-trimethyl]phenylcarboxy-2-methoxy-3,5,6-trimethyl benzoic acid (6c)

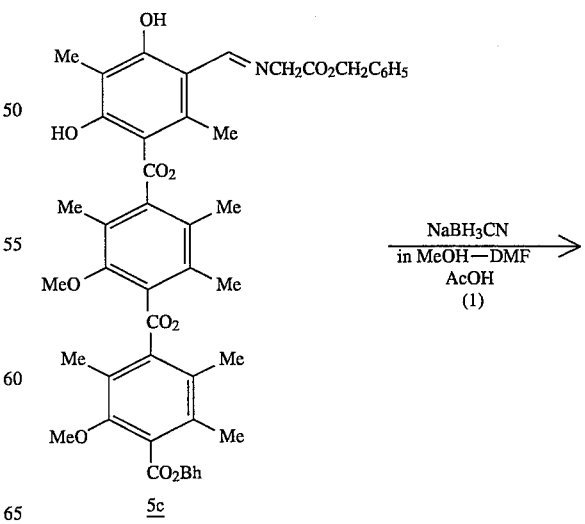

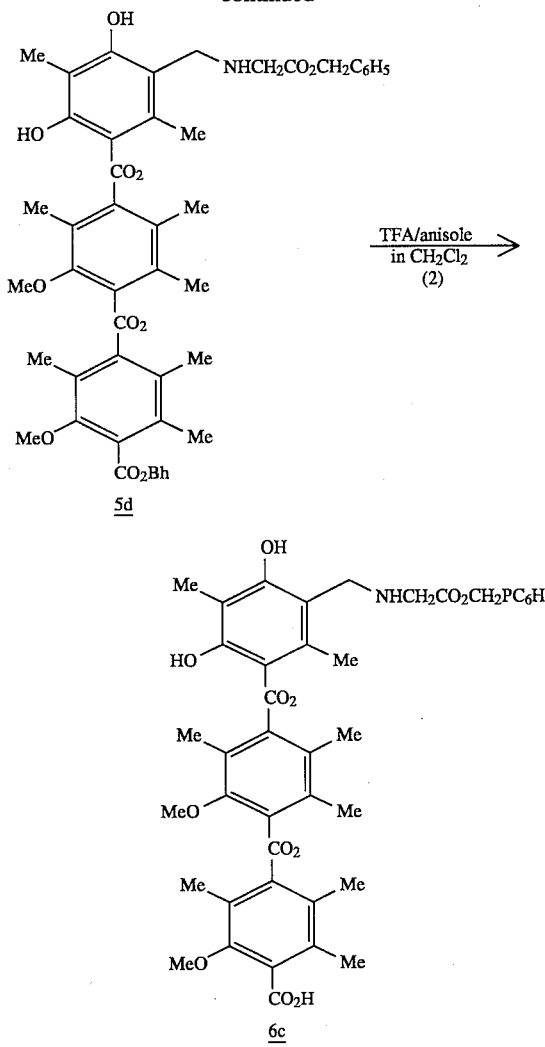

(1) Compound 5c (2.15 g, 2.37 mmol) obtained in the above step 1 was dissolved in 30 ml of dried dimethylformamide, and then 80 ml of dried methanol and 2 ml of acetic acid were added thereto. A solution of 0.3 g of sodium cyanoborohydride in 4 ml of methanol was added to the mixture in a stream of nitrogen, under cooling in a ice-bath over 15 minutes. The resulting mixture was directly stirred for three hours, and then allowed to stand overnight at 4° C. The methanol was evaporated in vacuo, and the residue was poured into cooled water. The mixture was acidified with 1N hydrochloric acid, and then basified with a saturated sodium bicarbonate solution. The precipitated crystals was collected by filtration, dissolved in 200 ml of ethyl acetate, and the solution was washed with 100 ml of brine, and dried over anhydrous sodium sulfate. The solvent was evaporated to yield 2.33 g of the yellow oil. The oil was subjected to silica gel chromatography ($SiO_2$; 120 g), eluting with ethyl acetate-n-hexane (1:2) to yield 1.07 g of 5d (the benzhydryl ester of the desired compound 6c) as a pale yellow oil (49.7%).

(2) Compound 5d obtained above (1 g, 1.1 mmol) was dissolved in 40 ml of dichloromethane, and then 0.6 ml (5.5 mmol) of anisole was added thereto. To the mixture was slowly added a solution of 0.85 ml (11 mmol) of trifluoroacetic acid in 4 ml of dichloromethane dropwise in an ice-cooling bath. The mixture was directly stirred for four hours, concentrated in vacuo, and 1N hydrochloric acid was added to the residue, and the precipitated solid was collected by filtration. The solid was washed with water repeatedly, dissolved in 50 ml of ethyl acetate, washed with 0.1% aqueous phosphate solution and with water, and then dried over anhydrous sodium sulfate. The solvent was evaporated to yield 865 mg of an yellow oil. The oil was subjected to silica gel chromatography ($SiO_2$; 50 g), eluting with chloroform-methanol (10:1), to yield 720 mg of 6c as an yellow oil (88.1%). This oil was recrystallized from 95% ethanol to yield 266 mg of the title compound 6c as pale yellow grained crystals, Mp: 134°–6° C. (dec.) Elementary Analysis (for $C_{41}H_{45}NO_{12} \cdot EtOH \cdot H_2O$) Theory: C;63.93, H;6.61, N;1.73 Found: C;63.90, H;6.58, N;1.81

Example 13

4-[5'-(Benzyloxycarbonylmethylaminomethyl)-2',4'-dihydroxy-3',6'-dimethyl]phenylcarboxy-2-methoxy-3,5,6-trimethyl benzoic acid (6')

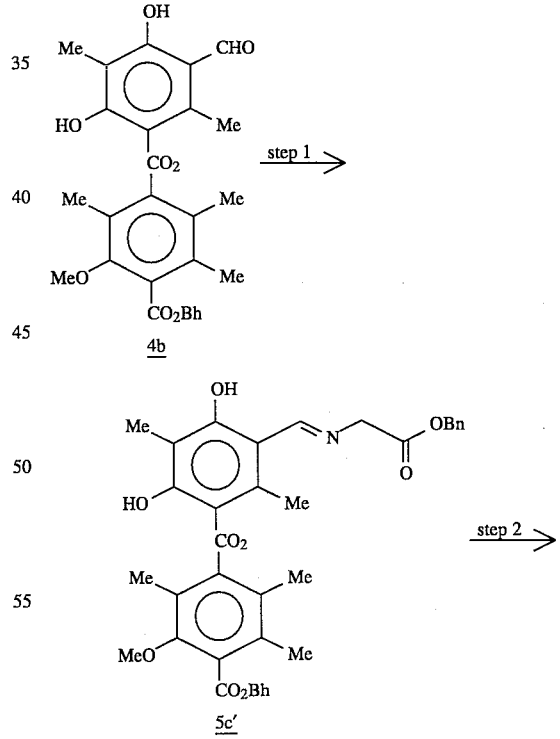

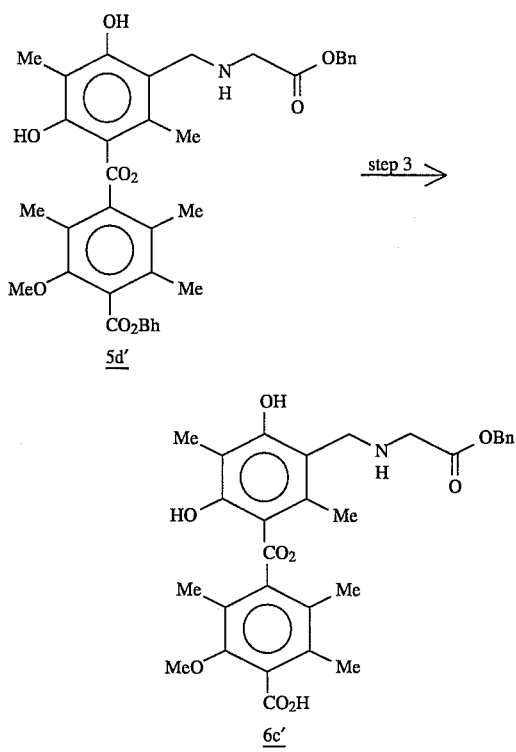

Step 1

Compound 4b (Preparation 1) (2.02 g, 3.5 mmol) was dissolved in 30 ml of DMF, and 5.98 g (17.7mmol) of Gly.OBn.Tos and 3.04 g (37 mmol) of sodium acetate were added thereto, and the mixture was stirred at room temperature. After completion of the reaction, 300 ml of water was added to the mixture, and the precipitated crystals was collected by filtration. The filtered cake was dissolved in ethyl acetate, and the solution was dried over $Na_2SO_4$, and the solvent was evaporated in vacuo to yield 2.33 g of benzhydryl 4-[5'-(benzyloxycarbonylmethyliminomethyl)-2',4'-dihydroxy-3',6'-dimethyl]phenylcarboxy-2-methoxy-3,5,6-trimethyl benzoate (5c').

5c'

$^1$H-NMR (δ,CDCl$_3$) 2.04 (3H, S), 2.08 (3H, S), 2.10 (3H, S), 2.15 (3H, S), 2.83 (3H, S), 3.55 (3H, S), 4.46 (2H, S), 5.24 (2H, S), 7.20 (1H, S), 7.23–7.50 (15H, m), 8.86 (1H, S), 11.95 (1H, S)

Step 2

Compound 5c obtained above (2.33 g, 3.25 mmol) was dissolved in 200 ml of a mixture of methanol and DMF (1:1). The mixture was cooled to 0° C., and a solution of 510 mg (8.1 mmol) of NaBH$_3$CN in 10 ml of methanol was added thereto dropwise, and then the mixture was stirred at 0° C. for 40 hours. To the mixture was added about 800 ml of ice water, and the precipitated yellow crystals was collected by filtration, which crystals were purified using 200 g of silica gel to yield 120 mg of benzhydryl 4-[5'-(benzyloxycarbonylmethylaminomethyl)-2',4'-dihydroxy-3',6'-dimethyl]phenylcarboxy-2-methoxy-3,5,6-trimethyl benzoate (5d').

5'

$^1$H-NMR (δ,CDCl$_3$) 2.03 (3H, S), 2.03 (3H, S), 2.08 (3H, S), 2.12 (3H, S), 2.54 (3H, S), 3.55 (3H, S), 4.11 (2H, S), 5.22 (2H, S), 7.20 (1H, S), 7.23–7.50 (15H, m), 11.60 (1H,S)

Step 3

Compound 5d' obtained above (120 mg, 0.167 mmol), and 97 mg (0.85 mmol) of anisole were dissolved in 6 ml of dichloromethane, and the solution was cooled to 0° C., and then, to the solution was slowly added 0.12 ml (1.64 mmol) of trifluoroacetic acid, and the mixture was stirred directly. After completing the reaction, the solvent was evaporated in vacuo, and 3 ml of 1N hydrochloric acid was added thereto, and the precipitated crystals was collected by filtration. The crystals was dissolved in ethyl acetate, and the solution was dried over sodium sulfate, and then the solvent was evaporated to yield the residue, which residue was purified using 75 g of silica gel. The resulting product (40 mg) was recrystallized from ethanol to yield 8.5 mg of the title compound 6C' as white crystals.

6c'

Mp: 164° C. IR (cm$^{-1}$, nujol): 3400–2300, 760, 1650, 1620. NMR (δ, CDCl$_3$-CD$_3$OD5%): 2.05 (3H, S), 2.09 (3H, S), 2.15 (3H, S), 2.29 (3H, S), 2.59 (3H, S), 3.69 (2H, S), 3.82 (3H, S), 4.23 (2H, S), 5.24 (2H, S), 7.36 (5H, S)

Preparation 1

Benzhydryl 4-[4'-(2",4"-dihydroxy-5"-formyl-3",6"-dimethylphenylcarboxy)-2'-methoxy-3',5',6'-trimethyl]phenylcarboxy-2-methoxy-3,5,6-trimethyl benzoate (4a), and benzhydryl 4-(5'-formyl-2',4'-dihydroxy-3',6'-dimethyl)phenylcarboxy-2-methoxy-3,5,6-trimethylbenzoate (4b)

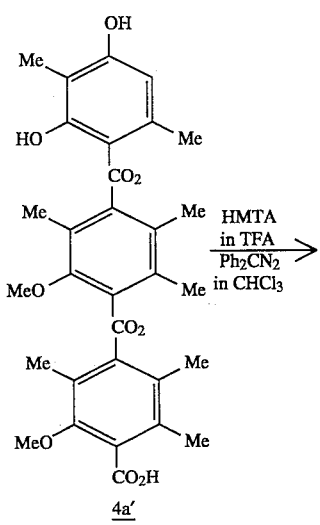

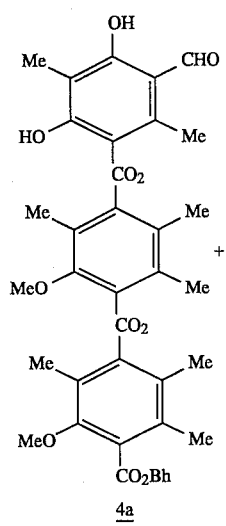

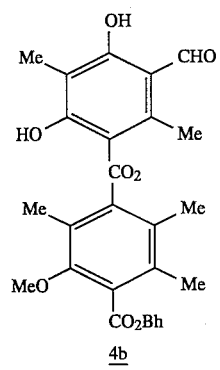

Thielavin B (Japanese Patent Application No. 162847/1991) (4a') (30 g, 53 mmol) was dissolved in 300 ml of trifluoroacetic acid, and 8.9 g (63 mmol) of hexamethylenetetraamine was added thereto in an ice-cooling bath, and the mixture was stirred for two hours. The mixture was warmed to room temperature, and was stirred for additional two hours, warmed at 50° C. for 4.5 hours, and then allowed to stand overnight at room temperature. The solvent, trifluoroacetic acid, was evaporated, and 400 ml of water was added thereto, and the mixture was heated at 60° C. for seven hours. The precipitated solid was collected by filtration, washed with water, dissolved in 300 ml of ethyl acetate, and washed with 1N hydrochloric acid, water and brine, and then dried over anhydrous sodium sulfate. The solvent was evaporated to yield 41.7 g of an orange foamy material, which material was dissolved in 200 ml of chloroform. To the solution was added 18 g (93 mmol) of benzhydryldiazomethane in an ice-cooling bath, and the mixture was stirred for 3.5 hours. The solvent was evaporated, and the residue was dissolved in 100 ml of ethyl acetate. The solution was washed with 1N hydrochloric acid, an aqueous saturated sodium bicarbonate solution, water, and brine, and then dried over anhydrous sodium sulfate. The solvent was evaporated to yield 46 g of an orange foamy material. The material was subjected to silica gel chromatographies (500 g and 400 g of $SiO_2$), eluting with ethyl acetate-n-hexane (1:4), and the same chromatography was repeated once more, to yield 9.95 g (24.7%) of Benzhydryl 4-[4'-(2",4"-dihydroxy-5"-formyl-3",6"-dimethylphenylcarboxy)-2'-methoxy-3',5',6'-trimethyl]phenylcarboxy-2-methoxy-3,5,6-trimethyl benzoate (4a), and 3.77 g (12.5%) of benzhydryl 4-(5'-formyl-2',4'-dihydroxy-3',6'-dimethyl)phenylcarboxy-2-methoxy-3,5,6-trimethylbenzoate (4b).

4b; white pillar crystals (ethyl acetate-n-hexane)

Mp; 182°–4° C. Elementary Analysis (for $C_{34}H_{33}O_8$ (MW: 569.604)) Theory: C;71.69, H;5.84 Found: C;71.61, H;5.77

Effect of the invention

The compounds of the present invention were tested for their Phospholipase $A_2$ inhibitory activity by the following procedure.

Method

1-Palmitoyl-2-[1-$^{14}$C]-linoleoyl L-3-Phosphatidylethanolamine (Amersham, Inc., 59 mCi/mmol) were diluted with L-α-phosphatidylethanolamine (Sigma, Co., from egg albumin) [2,000 dpm/nmol], and the dilution was sonicated. The resultant dilution was used as a substrate. The $PLA_2$ (phospholipase $A_2$) which was used in the test was from rat platelets. The $PLA_2$ and the substrate preparation were added to a solution of $CaCl_2$ (3 mM) in Tris-buffer (0.1M, pH 7.4), and the mixture was allowed to react at 37° C. for 20 minutes. Then, the reaction was terminated by adding 1.25 ml of Dole's reagent to the reaction mixture and stirring immediately the resultant mixture. To the mixture was added 0.5 ml of distilled water and 0.8 ml of n-heptane, and the mixture was stirred, centrifuged, and the resulting supernatant was taken into another tube. To this supernatant were added additional 0.8 ml of n-heptane and silica gel, and the mixture was stirred, centrifuged, and then the supernatant was taken into vials. Toluene cocktails were added to the vials. The amount of free fatty acid released from $PLA_2$ (DPM value) was determined using liquid scintillation counter.

Inhibitory activity (%) was estimated by the formula: [(DPM value at the addition of the inhibitor-DPM value without $PLA_2$)/(DPM value with only $PLA_2$-DPM value without $PLA_2$)]×100.

Results

The results are shown in the following Table 4.

TABLE 4

| PLA$_2$ inhibitory activity [IC$_{50}$(μM)] | |
| --- | --- |
| Compound No. | Rat platelets |
| 1a | 0.026 |
| 1b | 0.17 |
| 1c | 0.16 |
| 1d | 0.12 |
| 1e | 1.10 |
| 1f | 0.38 |
| 1g | 0.34 |
| 1i | 3.90 |
| 6b | 0.30 |

What is claimed is:

1. A compound of the formula:

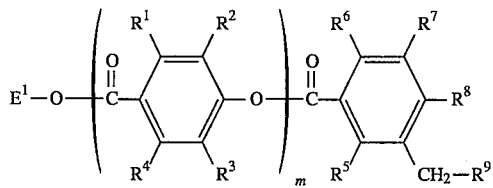

in which $R^1$, $R^2$, $R^3$, $R^4$, $R^5$, $R^6$, $R^7$ and $R^8$ are independently hydrogen; lower alkyl optionally substituted by one or more substituent(s) which are the same or different and which are selected from the group consisting of lower alkoxy, halogen, hydroxy, amino, phenyl, naphthyl, and anthryl; lower alkoxy optionally substituted by one or more substituent(s) which are the same or different and which are selected from the group consisting of lower alkyl, halogen, hydroxy, amino, and phenyl; hydroxy; acyloxy; or a halogen;

$R^9$ is lower alkylamino optionally substituted by one or more substituent(s) which are the same or different and which are selected from the group consisting of phenyl, an amino group of an urethane derivative, and a carboxyl group which may be esterified or amidated;

$E^1$ is hydrogen, or an ester residue;

m is an integer of from 1 to 4; or a pharmaceutically acceptable salt thereof.

2. The compound of claim 1 in which $R^9$ is a group which is selected from the group consisting of:

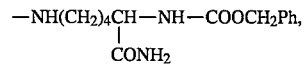

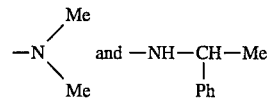

wherein Ph is a phenyl group which may have one or more substituents which are identically or differently selected from the group consisting of halogen lower alkoxy, hydroxy, amino and phenyl; or a pharmaceutically acceptable salt thereof.

3. A pharmaceutical composition comprising a compound or a pharmaceutically acceptable salt thereof as claimed in claim 1, in association with one or more pharmaceutically acceptable carriers or diluents therefore.

4. A method for treating a mammal suffering from or susceptible to any system caused by phospholipase A$_2$, which comprises administering to the mammal a therapeutically effective amount of the compound or pharmaceutically acceptable salt as claimed in claim 1.

* * * * *